US010624583B2

(12) United States Patent
Lemke et al.

(10) Patent No.: US 10,624,583 B2
(45) Date of Patent: Apr. 21, 2020

(54) REACTANCE SENSING FOR IMPROVED SENSOR PLACEMENT

(71) Applicant: Nonin Medical, Inc., Plymouth, MN (US)

(72) Inventors: David Lee Lemke, Victoria, MN (US); Patrick David Little, Champlin, MN (US); Douglas R. Maser, Rogers, MN (US); Jordan Clifford Welch Hartmann, Maple Grove, MN (US); Matthew Prior, Plymouth, MN (US)

(73) Assignee: Nonin Medical, Inc., Plymouth, MN (US)

( * ) Notice: Subject to any disclaimer, the term of this patent is extended or adjusted under 35 U.S.C. 154(b) by 304 days.

(21) Appl. No.: 13/673,888

(22) Filed: Nov. 9, 2012

(65) Prior Publication Data
US 2014/0135602 A1 May 15, 2014

(51) Int. Cl.
A61B 5/00 (2006.01)
A61B 5/01 (2006.01)
(Continued)

(52) U.S. Cl.
CPC .............. *A61B 5/6844* (2013.01); *A61B 5/01* (2013.01); *A61B 5/021* (2013.01); *A61B 5/0205* (2013.01); *A61B 5/02156* (2013.01); *A61B 5/0531* (2013.01); *A61B 5/08* (2013.01); *A61B 5/082* (2013.01); *A61B 5/145* (2013.01); *A61B 5/14551* (2013.01); *A61B 5/6824* (2013.01); *A61B 5/6826* (2013.01);
(Continued)

(58) Field of Classification Search
CPC .... A61B 5/00; A61B 5/04; A61B 5/08; A61B 5/02; A61B 5/14; A61B 5/6831; A61B 18/02; G01J 5/0022
USPC .............. 600/509, 322, 324, 595, 558, 549; 604/65
See application file for complete search history.

(56) References Cited

U.S. PATENT DOCUMENTS 6,015,390 A * 1/2000 Krag ...................... A61B 18/02
128/DIG. 27
6,312,393 B1 * 11/2001 Abreu .................. A61B 3/1241
600/558

(Continued)

FOREIGN PATENT DOCUMENTS

JP 2008-104666 A 5/2008
JP 2009222704 A 10/2009

(Continued)

OTHER PUBLICATIONS

"International Application Serial No. PCT/US2013/069185, International Search Report dated Mar. 26, 2014", 3 pgs.

(Continued)

*Primary Examiner* — Lynsey C Eiseman
*Assistant Examiner* — Jonathan T Kuo
(74) *Attorney, Agent, or Firm* — Schwegman Lundberg & Woessner, P.A.

(57) ABSTRACT

A sensor assembly which includes a first physiological parameter sensor configured to sense a physiological parameter and a first reactance sensor connected to the first physiological parameter sensor. The first reactance sensor provides a signal corresponding to a position of a tissue relative to the first reactance sensor and corresponding to the first physiological parameter sensor.

16 Claims, 12 Drawing Sheets

(51) Int. Cl.
*A61B 5/0205* (2006.01)
*A61B 5/0215* (2006.01)
*A61B 5/08* (2006.01)
*A61B 5/1455* (2006.01)
*A61B 5/021* (2006.01)
*A61B 5/053* (2006.01)
*A61B 5/145* (2006.01)

(52) U.S. Cl.
CPC .......... *A61B 5/6829* (2013.01); *A61B 5/6831* (2013.01); *A61B 5/6833* (2013.01); *A61B 5/7221* (2013.01)

(56) References Cited

U.S. PATENT DOCUMENTS

| | | | |
|---|---|---|---|
| 7,976,492 B2* | 7/2011 | Brauker | A61B 5/0002 604/31 |
| 8,428,683 B2 | 4/2013 | Yoo et al. | |
| 8,521,262 B2* | 8/2013 | Webler | A61B 5/042 600/508 |
| 2003/0132763 A1 | 7/2003 | Ellenz | |
| 2005/0245839 A1* | 11/2005 | Stivoric | G06F 19/3418 600/549 |
| 2005/0281441 A1* | 12/2005 | Martinsen | A61B 5/0531 382/124 |
| 2007/0073123 A1 | 3/2007 | Raridan, Jr. | |
| 2008/0027350 A1* | 1/2008 | Webler | A61B 5/042 600/547 |
| 2008/0167539 A1 | 7/2008 | Teller et al. | |
| 2008/0232604 A1 | 9/2008 | Dufresne et al. | |
| 2009/0240163 A1* | 9/2009 | Webler | A61B 5/042 600/547 |
| 2010/0094107 A1* | 4/2010 | Lamego | A61B 5/061 600/322 |
| 2010/0210924 A1 | 8/2010 | Parthasarathy et al. | |
| 2011/0105910 A1 | 5/2011 | Lawson et al. | |
| 2012/0177083 A1* | 7/2012 | Lin | G01J 5/0022 374/121 |
| 2013/0183646 A1* | 7/2013 | Lusted | G09B 19/00 434/236 |
| 2013/0338447 A1* | 12/2013 | Gilad-Gilor | A61B 5/0077 600/300 |

FOREIGN PATENT DOCUMENTS

| | | | | |
|---|---|---|---|---|
| JP | 2012-024391 A | 2/2012 | | |
| JP | WO 2012014691 A1 * | 2/2012 | ............... | A61B 5/01 |
| KR | 1020100126107 A | 12/2010 | | |
| WO | WO-0056209 A1 | 9/2000 | | |
| WO | WO-2007087529 A2 | 8/2007 | | |
| WO | WO-2014/074843 A1 | 5/2014 | | |

OTHER PUBLICATIONS

"International Application Serial No. PCT/US2013/069185, Written Opinion dated Mar. 26, 2014", 7 pgs.
International Application Serial No. PCT/US2013/069185, International Preliminary Report on Patentability dated May 21, 2015, 9 pgs.
European Application Serial No. 13852630.6, Office Action dated Jul. 9, 2015, 2 pgs.
European Application Serial No. 13852630.6, Response filed Jan. 15, 2016 to Office Action dated Jul. 9, 2015, 8 pgs.
Japanese Application Serial No. 2015-541931, Office Action dated 09-12-172898-081, (W/English translation), 9 pgs.
European Application Serial No. 13852630.6, Extended European Search Report dated Jun. 28, 2016, 11 pgs.
European Application Serial No. 13852630.6, Response filed Jan. 24, 2017 to Extended European Search Report dated Jun. 28, 2016, 14 pgs.
Canadian Application Serial No. 2,890,715, Office Action dated Sep. 13, 2019, 3 pgs.
European Application Serial No. 13852630.6, Communication Pursuant to Article 94(3) EPC dated May 3, 2019, 5 pgs.

* cited by examiner

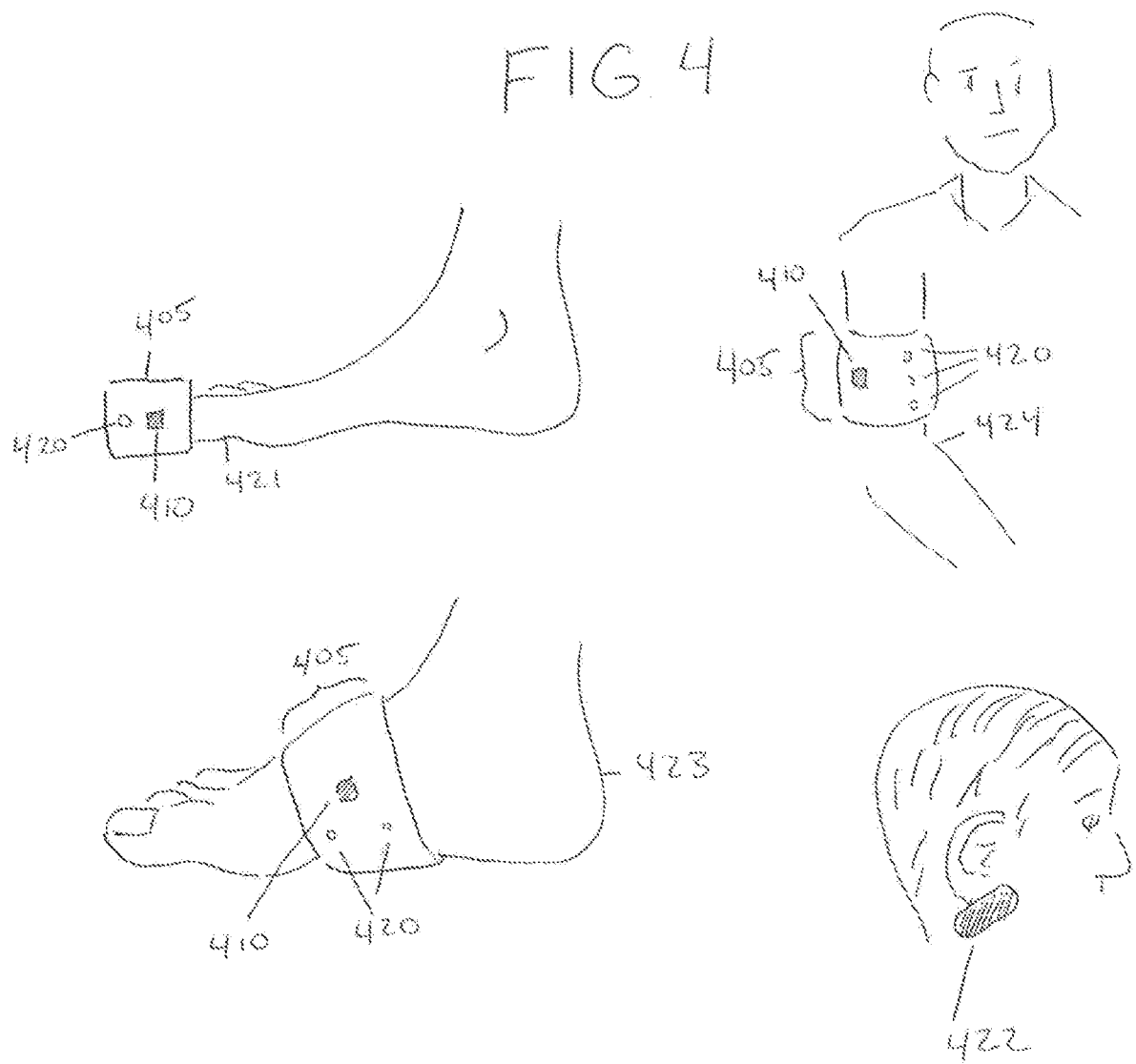

1100

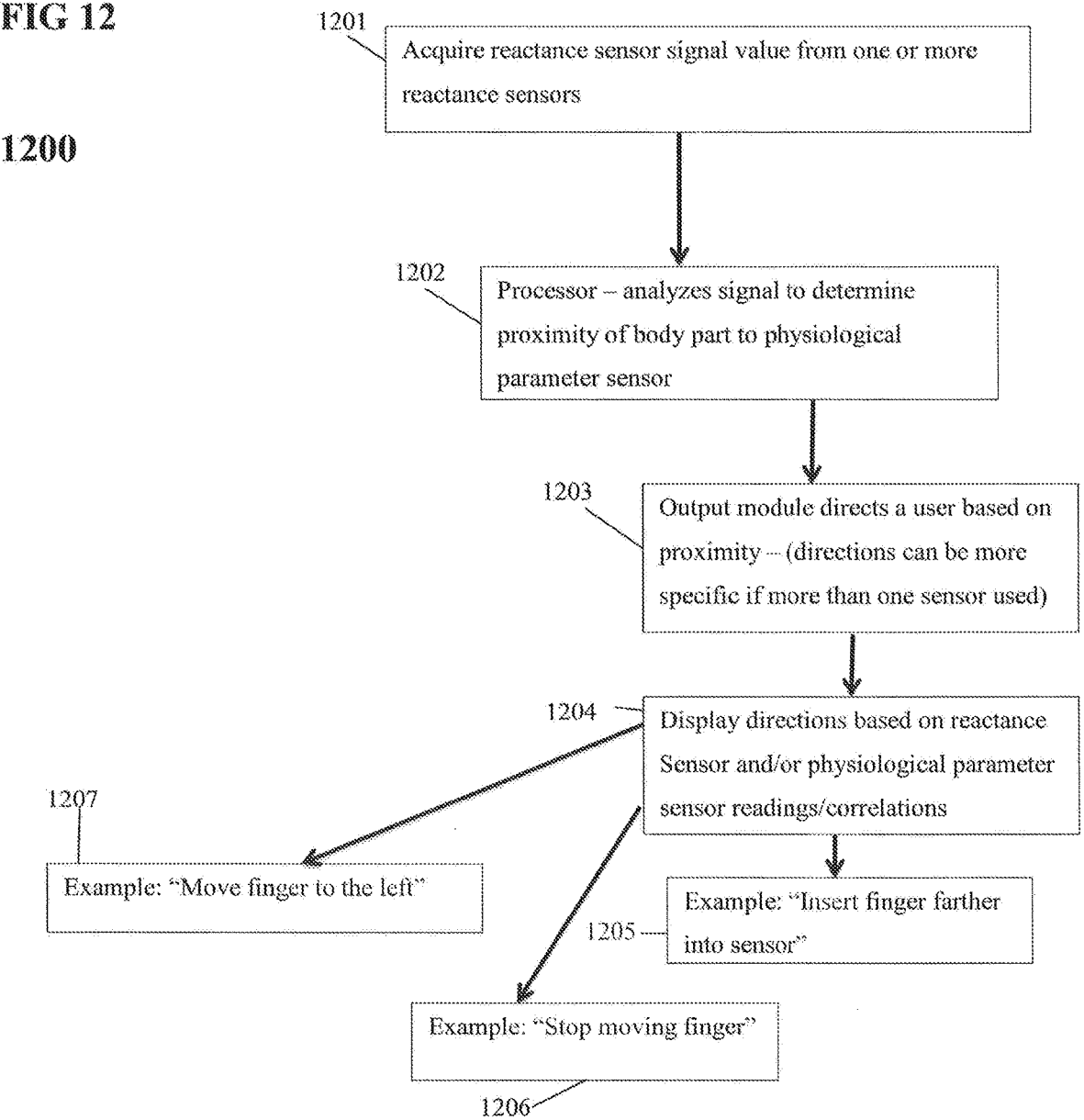

REACTANCE SENSING FOR IMPROVED SENSOR PLACEMENT

BACKGROUND

Physiological parameter sensors can perform a wide variety of functions including but not limited to detecting: pulse, saturated oxygen content of blood, blood pressure, body temperature, blood analyte concentrations, respiratory gas concentrations, and breathing rates. Physiological parameter sensors can take a wide variety of forms depending on the size and species of a body being measured, the area of the body being sensed and the type of sensing being conducted. Pulse oximetry sensing measures the saturated oxygen content of arterial blood. Pulse oximetry sensors can be positioned on fingers, toes, ear lobes, and also on flatter body parts such as the forehead or chest. In order to fit various body parts, pulse oximetry sensors are produced in a wide variety of forms. Capnography sensors measure the amount of $CO_2$ in respiratory gases. Normally a body is fit with a re-breather type of face mask or a nasal cannula. Some of these sensor forms require correct positioning in order to ensure proper functioning. Existing physiological parameter sensor systems do not provide automatic sensing of the presence, position, location, size, or movement of a body part. In modern clinics and hospitals many physiological parameter parameters are measured remotely, and a sensor alarm indicating that the sensor has moved or slipped out of position would be very useful. A sensing system with the ability to indicate a presence of a body part in a sensor and a correct position of the body part relative to the sensor would provide increased accuracy and improved functioning. In addition, sensing of the position of a body part relative to the sensor could be used to provide feedback to the user to obtain optimal sensor placement.

OVERVIEW

This document pertains generally, but not by way of limitation, to physiological parameter sensors. More specifically the present invention relates to proximity/presence sensing used in conjunction with physiological parameter sensors (e.g., pulse oximetry sensors). Capacitance or inductance sensing can provide a physiological parameter sensor with means to detect the presence, proximity, location, size, movement, and positioning of a body part associated with the physiological parameter sensor.

The present subject matter addresses problems relating to physiological parameter sensors. These sensors fit on or over body parts. Correct positioning and adjustment can provide an improved signal. Remote monitoring of such sensors can be greatly aided by alarm notification when the sensor is out of position. Humans and most animals have electrically conductive bodies. Capacitance sensing is a technology that senses changes in an electric field emanating from a sensor electrode. Changes in the electric field of a capacitance sensor can be produced by the proximity of an electrically conductive body part (e.g., a finger). Inductance sensing is similar to capacitance sensing but instead of sensing changes in an electric field, changes in a magnetic field are sensed. These two types of sensing fall under the umbrella of "reactance" sensing. In the following disclosure it should be recognized that both inductance sensing or capacitance sensing or a combination of both types of sensors can constitute reactance sensing. Reactance sensing can provide a physiological parameter sensing system with the means to detect the presence, proximity, location, size, movement, and positioning of a body part associated with the physiological parameter sensor. Presence and positional sensing can allow a physiological parameter sensor to change operating modes (e.g., power up/down, etc.) automatically when the reactance sensor detects the proper signal.

One type of physiological parameter sensor, a pulse oximetry sensor, can gain several advantages by being powered up when a finger is inserted into the device. Processors and output devices connected to the physiological parameter sensor can remain on a standby mode and conserve energy, but ready to power up when a body part is inserted. Another advantage to this approach is that using reactance sensing for automatic power up can eliminate an infrared (IR) signature when the sensor system is in a standby mode. It is an advantage to keep a sensor assembly in a standby mode because it can very quickly be switched to a powered up mode. To maintain an assembly in a powered up mode when not actively in use, can generate infrared or other types of electrical/magnetic energy which may interfere with other medical devices.

The reactance sensor generates a signal which may vary in signal quality, signal strength, and other parameters regarding the signal. A sensor assembly can process the reactance signal to determine if it has met a minimum threshold value. If the signal has met a minimum threshold value a processor can instruct a device to proceed to physiological parameter sensing. If a threshold value has not been met, the processor can instruct the device to enter a standby mode. The threshold values can be fixed or dynamic. A dynamic threshold lookup table can be updated or recalculated based on a quality determination of the physiological parameter sensor output.

In addition to sensing presence of a body part in a sensor system with a physiological parameter sensor, a reactance sensing system can give a more accurate picture of how and where a body part is located within the sensor system. It can be imperative in some physiological parameter sensors that a body part is in a proper position. For example, in a fingertip pulse oximetry sensor, the finger needs to be fully inserted into a sensor housing to provide reliable output signals. In a sensor system in which one reactance sensor is used, a sensor can be placed at the distal end of a sensor. If a body part has not been inserted or placed into close enough proximity to the reactance sensor, the sensor assembly can generate an alarm or be precluded from a power-up sequence. If more than one reactance sensor is used; more complex positioning information can be generated. For example, a physiological parameter sensing system can have reactance sensors configured so that if a body part is not sensed, or only partially sensed by one or more of the reactance sensors, then the body part is not in the correct position relative to a physiological parameter sensor. With multiple reactance sensors, a processor can determine whether a body part is off to one side of the sensing system and whether or not the sensor needs to be repositioned for an accurate reading. With a reactance sensor, a processor can send information through an output device to assist the user in finding the optimal sensor location.

In many physiological parameter sensing applications, it is important to know whether or not the body part sensed (e.g., a finger) is moving during physiological parameter sensing. Movement of body parts can cause motion artifacts and send an inaccurate electrical signal to a processor. A more accurate output of information can be created if signals known to be inaccurate are ignored or compensated. Movement sensing can also provide information to a processor to determine when to begin sensing. For example, a patient or caregiver might be in the process of adjusting a sensor system. With reactance sensing, a sensor system can inform a processor not to begin data collection until movement ceases. A system can be configured to detect subtle movements of the body part by evaluating a change in pressure on the body part. This can be accomplished in a number of ways including measuring a flatness of a body part (e.g., finger flatness). Motion detection algorithms can be developed to benefit from a more precise detection of any body part movement during physiological parameter sensing.

A patch type sensor should be closely attached to a patient. Air gaps between a patch sensor and a patient can produce a large change in reactance. A reactance sensing system can indicate whether a patch type sensor has partially or fully lifted from the skin of a patient. Patch type sensor assemblies are generally planar when applied and are used on foreheads, chest, abdomens and any other body part where a patch type sensor is appropriate. This can be any type of sensor that has a planar planform.

Sensor assemblies can be made to fit a wide assortment of body parts for various reasons. Fingertip sensing is widely used; however in some circumstances a finger might not be available for sensing purposes. Physiological parameter sensing can be accomplished on ear lobes, feet, toes, arms, wrists and other body parts. A sensor housing must be manufactured to fit these applications. In some applications a different body part might produce more accurate sensing signals. For example a person might have such poor peripheral circulation that a chest sensor would produce a more accurate physiological sensing signal than a fingertip sensor.

Some physiological parameters can be dependent on the size of a body part. For example, smaller fingers may tend to cool more rapidly than larger fingers. In another example, the size of a body part can have an effect on light transmittance and scattering in a pulse oximeter. A reactance sensing system with a particular configuration of reactance sensors can determine the size of a body part. This information can be provided to a processor and appropriate algorithms can compensate for size differences and produce a more accurate output signal.

The reactance sensing system may have the reactance sensors in the form of a phased array. In a phased array, a phase controller can vary the phase of the transmitted signal and provide greater signal discrimination among an array of sensors. An array can constitute two or more reactance sensors.

The reactance sensing system can have a processor which can analyze sensing data from one or more reactance sensors regarding presence, proximity, location, size, movement, and positioning of a body part and correlate this data to data obtained from one or more physiological parameter sensors to optimize the output of physiological parameter information. For example, in a pulse oximetry sensor an accurate reading of oxygen saturation could be obtained if a finger was absolutely still and in a perfect position. For illustration purposes only: an accurate reading of a perfectly placed non-moving finger might read 99% saturation. If the same finger was not placed perfectly or was moving—an unprocessed physiological parameter signal output might read only 85%. Through the use of algorithms relating to movement or position the processor could still produce an accurate physiological parameter output reading. The algorithms would take into account the data provided by one or more reactance sensors and depending on how much movement was detected or how far from a perfect position in relation to the physiological parameter sensor the body part was placed; a processor can compensate the received physiological parameter signal to produce an accurate output reading.

The reactance sensing system can have software associated with the device to provide means of interpreting an electrical signal from the reactance sensing circuit. This software can determine thresholds of the changes in the electrical field and control machine behavior. For example, after a processor receives reactance sensing signals, a software program can instruct the processor to compare this information to stored information. Depending on the comparison, the program can instruct the processor whether or not to reset a baseline reading for the physiological parameter sensor based on the positioning of the body part. The results of the processed information can also determine how the processor is to respond in the event a body part is present in the physiological parameter sensor when the unit is turned on, or turn off in response to the removal of the sensor from the proximity of a body part. The reactance sensor can work in conjunction with the physiological sensor and processor through feedback loops which can continually improve the quality of the physiological sensor output as the body part is moved towards an optimal positioning.

In the present invention, a sensor system includes at least one physiological parameter sensor and at least one reactance sensor. The sensor system can also include a processor and an output module. The physiological parameter sensor can sense one or more of the following, pulse, saturated oxygen content of tissue or blood, blood pressure, body temperature, blood analyte concentrations, respiratory gas concentrations, and breathing rates. The physiological parameter sensor can take many physical forms including but not limited to, a fingertip sensor, a toe sensor an ear lobe sensor, a wrist sensor, an arm sensor, a leg sensor, a patch type sensor, a re-breather mask, a somatic patch, or a cannula. The reactance sensor in connection with a physiological parameter sensor can sense the presence, proximity, location, size, movement, and position of a body part associated with the physiological parameter sensor. Depending on the parameters of the body part sensed, a processor can initiate a power up sequence, an alarm sequence, a resetting sequence, a shutdown sequence, and provide pertinent information such as calibration information, to the output module.

This section is intended to provide an overview of the present subject matter. It is not intended to provide an exclusive or exhaustive explanation of the invention. The detailed description is included to provide further information about the present patent application.

To better illustrate the assemblies, systems, methods and software disclosed herein a non-limiting list of examples is provided. These non-limiting examples can be combined in any permutation or combination.

Example 1 includes a sensor assembly having first physiological parameter sensor configured to sense a physiological parameter; and a first reactance sensor connected to the first physiological parameter sensor wherein the first reactance sensor provides a signal corresponding to a position of a tissue relative to the first reactance sensor and corresponding to the first physiological parameter sensor.

In Example 2, the subject matter of Example 1 can optionally include: a processor coupled to the first physiological parameter sensor and coupled to the first reactance sensor, the processor configured to generate an output based on the physiological parameter and the position; and an output module coupled to the processor, the output module configured to provide a measure corresponding to the physiological parameter.

In Example 3, the subject matter of one or any combination of Examples 1-2 and can optionally include sensor assembly wherein the first physiological parameter sensor is configured to be controlled by signals generated by the reactance sensor. This can be accomplished in one of several means: for example 1) if the reactance signal has met a low threshold, the physiological parameter signal can be adjusted in accordance with the low threshold value reactance signal, 2) if the reactance signal has met an intermediate threshold value, the physiological parameter signal can be adjusted in accordance with an intermediate threshold value, and 3)) if the reactance signal has met a high threshold value, the physiological parameter signal can be adjusted in accordance with a high threshold value. The control of the physiological parameter signal may also be accomplished by using algorithms. If the reactance sensor signal is indicative of movement of a tissue, the physiological parameter signal can be processed with algorithms correcting for movement to output a more accurate signal.

In Example 4, the subject matter of one or any combination of Examples 1-3 and can optionally include a sensor system further including a second reactance sensor coupled to the first physiological parameter sensor.

In Example 5, the subject matter of one or any combination of Examples 1-4 and can optionally include a sensor system wherein the first reactance sensor and the second reactance sensor are in fixed positions relative to the first physiological parameter sensor.

In Example 6, the subject matter of one or any combination of Examples 1-5, a sensor system can optionally include a second physiological parameter sensor coupled to the first reactance sensor.

In Example 7, the subject matter of one or any combination of Examples 1-6 and can optionally include a sensor system wherein the physiological parameter sensor includes at least one of a pulse oximetry sensor, a body temperature sensor, a blood pressure sensor, a blood analyte sensor, a respiratory rate sensor, a capnography sensor.

In Example 8, the subject matter of one or any combination of Examples 1-6 and can optionally include a sensor system wherein the physiological parameter sensor is a multifunction sensor which can measure any combination of pulse, saturated oxygen content, blood pressure, body temperature, blood analyte concentration, respiratory gas concentration, and breathing rates.

In Example 9, the subject matter of one or any combination of Examples 1-8 can optionally include a sensor system wherein the sensor assembly includes at least one of a fingertip sensor, a toe sensor, an ear lobe sensor, an arm sensor, a wrist sensor and a foot sensor.

In Example 10, the subject matter of one or any combination of Examples 1-8 can optionally include a sensor system wherein the sensor assembly has a planar planform.

In Example 11, the subject matter of one or any combination of Examples 1-10 can optionally include a sensor system wherein the first reactance sensor includes at least one of a capacitor and an inductor.

In Example 12, the subject matter of one or any combination of Examples 1-11 can optionally include a sensor system wherein the sensor assembly includes an array of reactance elements.

Example 13 includes a non-transitory computer readable medium comprising machine readable information for causing a machine to: read physiological parameter sensor data and reactance sensor data; and output physiological parameter data corresponding to a tissue wherein the physiological parameter data corresponds to a position of a reactance sensor in relation to a position of the tissue.

Example 14 includes the computer readable medium of Example 13 and can optionally include a computer readable medium configured to: compare the reactance sensor data to a threshold value; and determine a position of a sensor assembly relative to the tissue based on the comparison.

Example 15 includes the computer readable medium of Examples 13-14 and can optionally include a computer readable medium wherein the computer readable medium is configured to: compare the reactance sensor data to a threshold lookup table; compare the physiological parameter sensor data with a stored value; and generate a result based on the comparison of the reactance sensor data and the comparison of the physiological parameter sensor data.

Example 16 includes method of using a sensor assembly comprising: generating a reactance sensing signal, including determining at least one of a presence, a position, a movement, a size, or a proximity of a body part relative to a physiological parameter sensor; determining a value of the reactance sensing signal; comparing the reactance sensing signal to a threshold value; and based upon the comparing, generating a physiological parameter sensor signal indicative of at least one of pulse, saturated oxygen content, blood pressure, body temperature, blood analyte concentration, respiratory gas concentration, and breathing rate.

In Example 17 the subject matter of Example 16 can optionally include a method further comprising determining a quality of the physiological parameter sensor signal.

In Example 18 the subject matter of one or any combination of Examples 16-17 can optionally include a method further comprising setting a threshold value for the reactance sensing signal using information about the determined quality of the physiological parameter sensor signal.

In Example 19 the subject matter of one or any combination of Examples 16-18 can optionally include a method further comprising setting a mode of operation of the sensor assembly using information about the determined value of the reactance sensing signal.

In Example 20 the subject matter of one or any combination of Examples 16-19 can optionally include a method further comprising altering the physiological parameter sensor signal using information about the reactance sensing signal.

In Example 21 the subject matter of one or any combination of Examples 16-20 can optionally include a method further comprising providing a user-detectable indication of sensor assembly location relative to a body part of interest based upon the comparison between the reactance sensing signal and the threshold value.

Example 22 includes the subject matter of Example 13 and optionally the subject matter of Examples 1-12 or Examples 16-21.

Example 24 includes the subject matter of Example 16 and optionally the subject matter of Examples 1-15.

In Example 25 a method of using a sensor assembly comprising: generating a reactance sensing signal to determine the presence, position, movement, size or proximity of a body part relative to a physiological parameter sensor, wherein a reactance sensor is operatively connected to a processor and an output module; generating a physiological parameter sensing signal, wherein a physiological parameter sensor is operatively connected to a processor and an output module; processing the reactance sensing signal and the physiological parameter sensing signal to provide an output signal.

These non-limiting examples can be combined in any permutation or combination.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 4 illustrates an isometric view of optional locations of a sensor (e.g., toes, feet, and arm).

FIG. 12 illustrates a method or software flowchart showing system operations.

DETAILED DESCRIPTION

Figure 1:
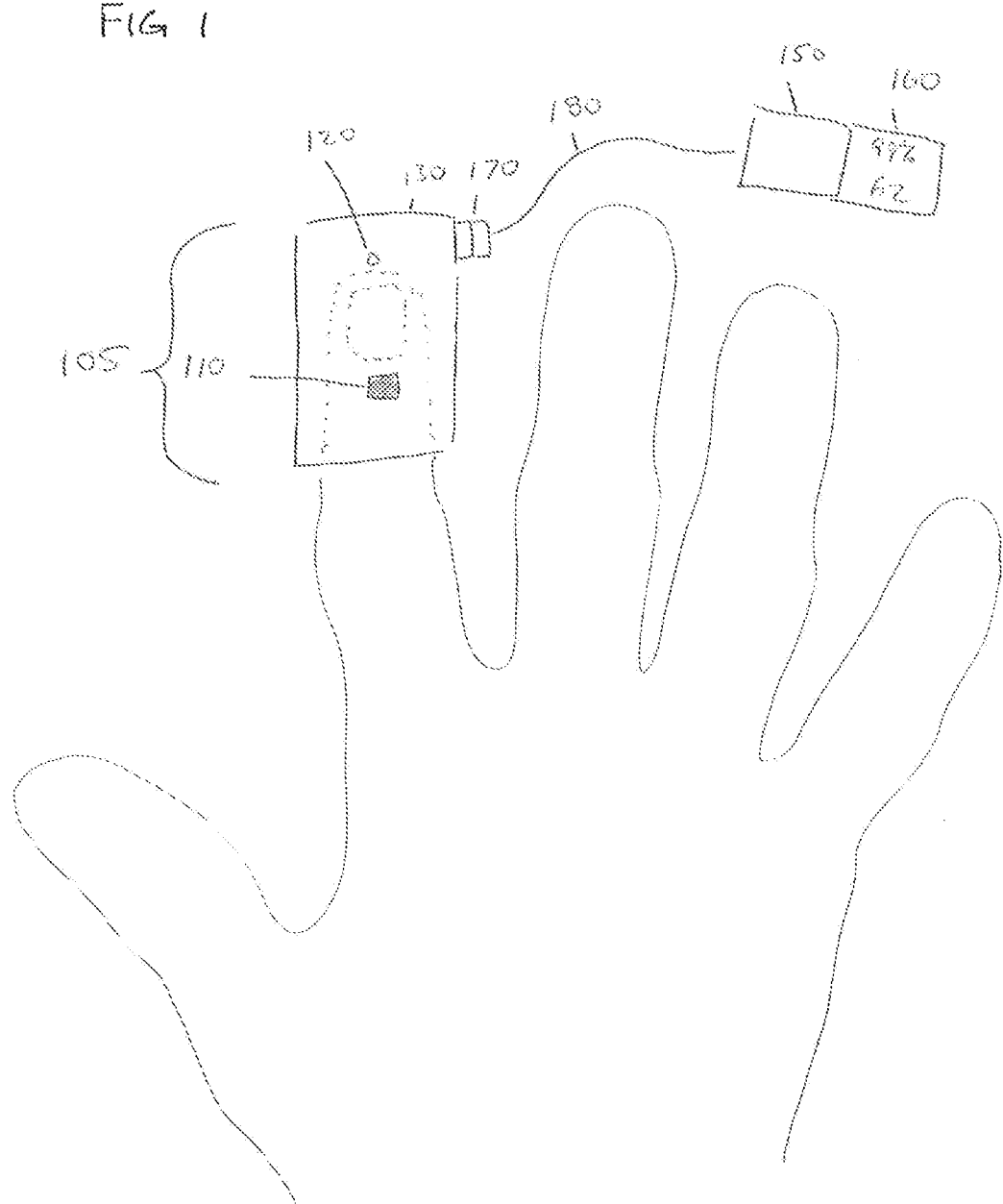
FIG. 1 illustrates placement of a sensor assembly on a finger.

FIG. 1 illustrates a sensing system (105). A sensing system housing (130) can be fabricated of a wide variety of materials including but not limited to fabric, foam, metal or plastic. It can be shaped in a broad variety of ways depending on what body part is being sensed. Sensor housings may be configured to flex, retain their shape, or can be rigid. Sensor housings can be used on various body locations. (e.g., finger, toe, ear lobe, chest, or forehead). Sensor housings can be used on multiple body parts (e.g., a finger and a toe, or a calf and the forehead). A physiological parameter sensor (110) is configured in a location where the type of sensing is appropriate. In another example, a pulse oximeter sensor can be placed in a location and sensing direction which will provide the most advantageous illumination of blood flow. A reactance sensor (120) can be configured at a location where a minimal amount of body part proximity must be provided to gain an accurate physiological parameter sensing signal. For example in a sensing system housing in which a finger is inserted, a reactance sensor near the distal end of the housing would ensure that the finger was inserted to that distance before a power up signal or a measuring signal was initiated by a processor (150). FIG. 1 also illustrates a connecting cable (170) and wiring (180) connecting the sensors to the processor (150). The sensor, processor, and an output module (160) can be one integrated unit or separate and connected. The sensor can communicate wirelessly with a remote processing unit.

Figure 2:
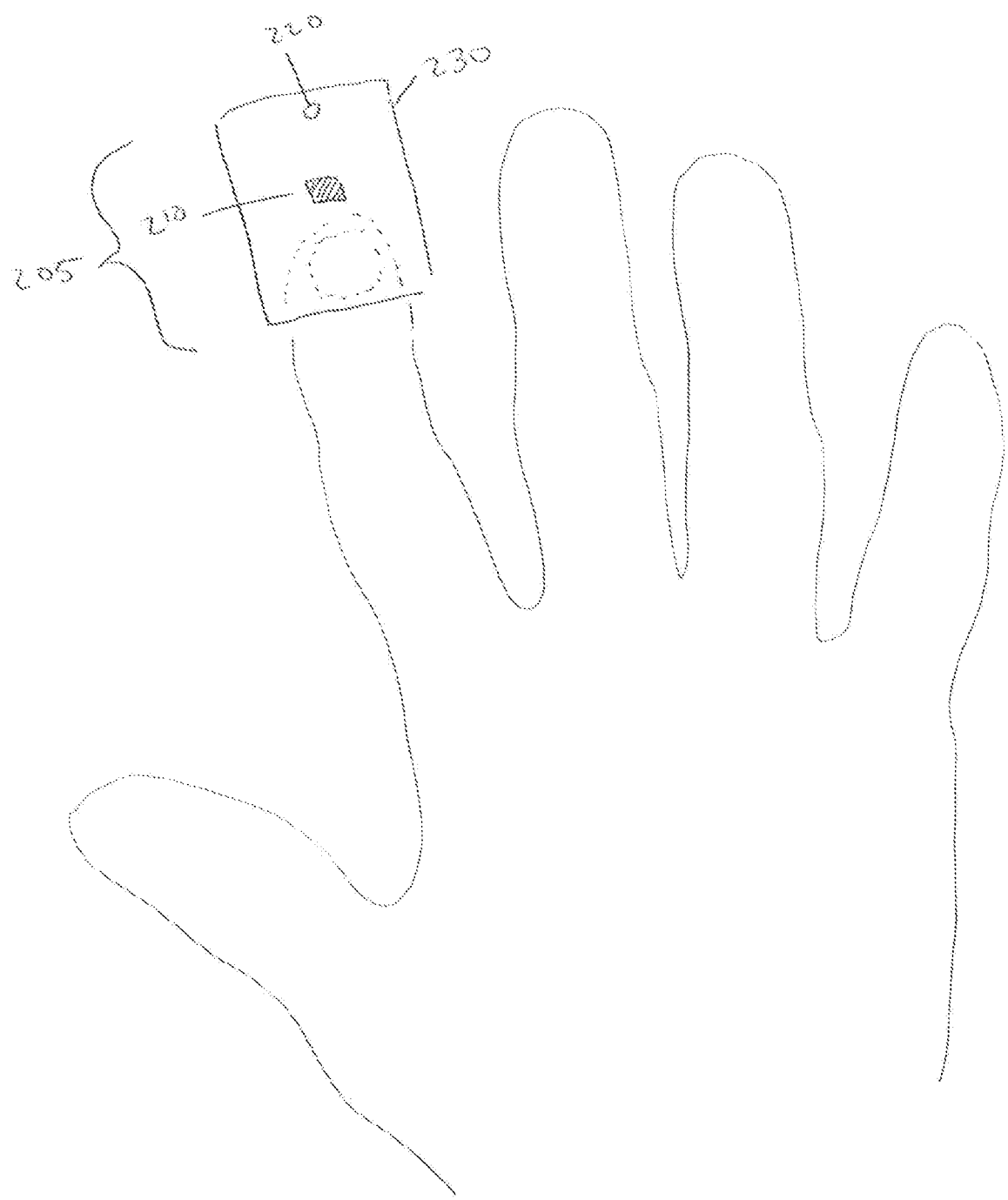
FIG. 2 illustrates incorrect placement of a finger relative to a sensor.

FIG. 2 illustrates a sensor system (205) in which a body part (e.g., finger) is not positioned sufficiently far into the sensor system housing (230). In this position, the reactance sensor (220) will not generate a signal indicating a proper placement of the body part in relation to the physiological parameter sensor (210).

Figure 3:
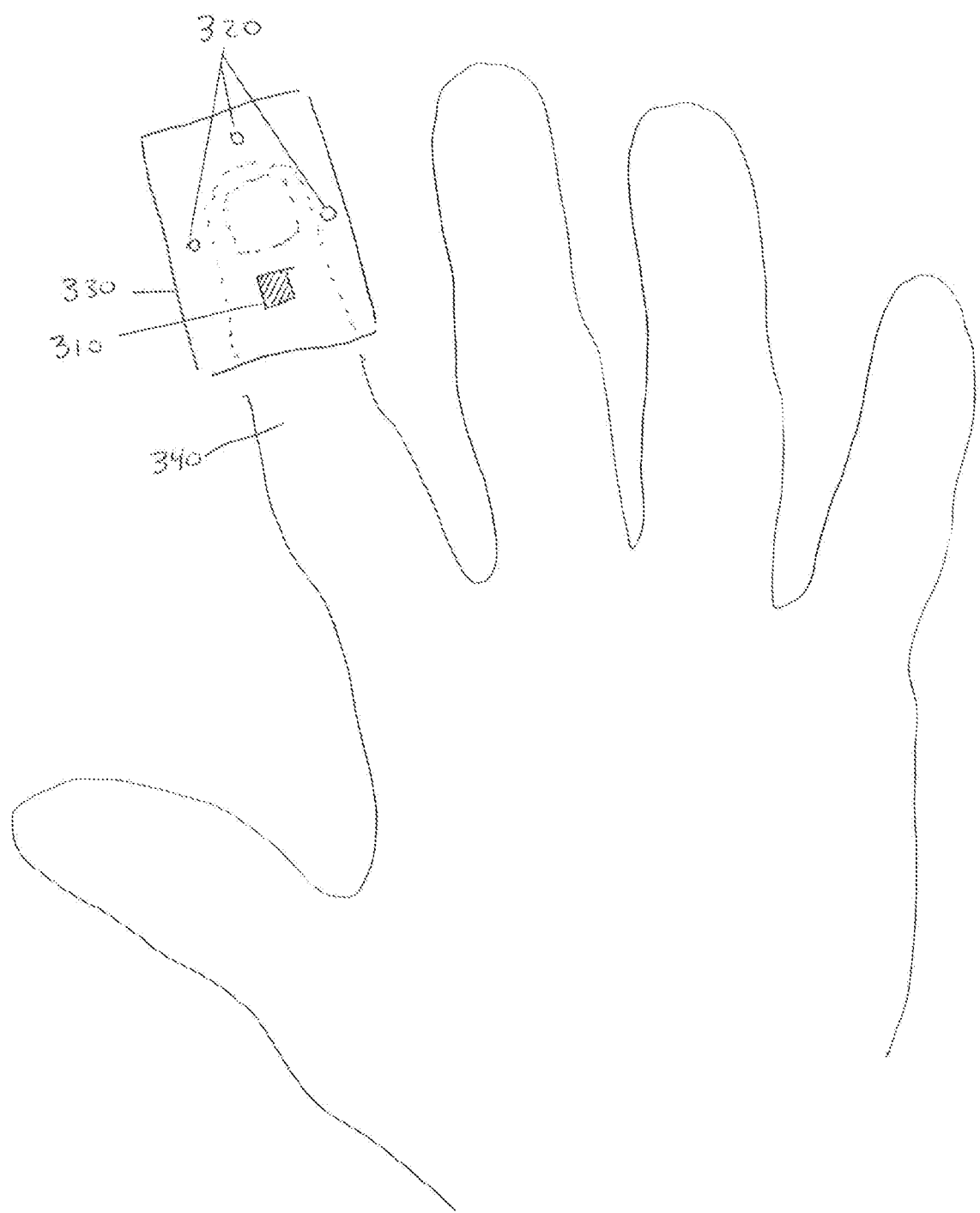
FIG. 3 illustrates a plan view of a sensor and location of multiple reactance sensors.

FIG. 3 illustrates a sensing system having multiple reactance sensors (320). The sensors can be configured to provide information regarding the orientation of the body part (340) within the sensor housing (330). The reactance sensors can be configured to collect movement information and can be placed in areas of the system that are most prone or affected by movement (e.g., near the tip of a body part which might not be as stationary as a proximal end of a body part). The physiological parameter sensor (310) is shown.

FIG. 4 shows sensor systems (405) and locations of reactance sensors (420) and physiological parameter sensors (410) in several configurations: a toe (421); an ear lobe (422), an arm (424), and a foot (423).

Figure 5A:
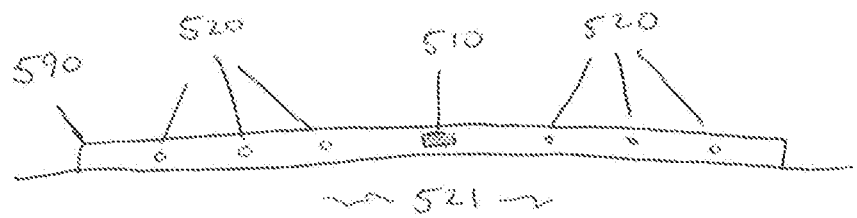
FIG. 5a illustrates a cross sectional view of a patch sensor lying flat against a body.
Figure 5B:
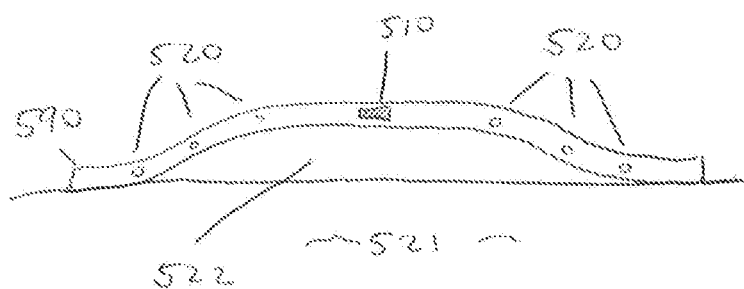
FIG. 5b illustrates cross sectional view of a patch sensor with an air gap.
Figure 5C:
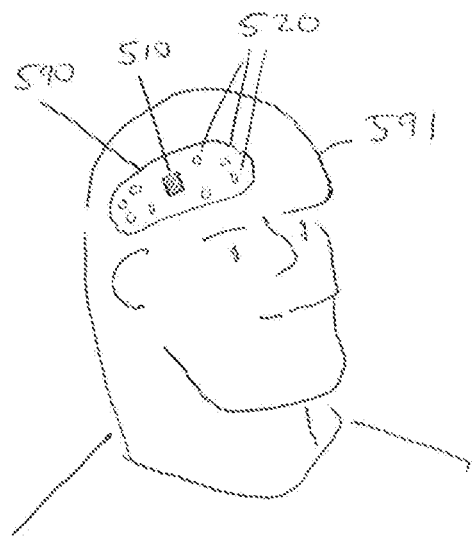
FIG. 5c illustrates an isometric view of a patch in place on a head.

Patch sensors can be utilized on wide or flat areas of a body such as the head, chest or back as well as other areas of a body. FIG. 5c shows a patch sensor (590) placement on a head (591). The distribution of several reactance sensors (520) will ensure that the patch sensor remains close to the surface of the body. FIG. 5a shows a patch sensor (590) in cross section lying flat against a body (521). The reactance sensors (520) will provide a signal indication that the sensor (590) is close to the body. FIG. 5b indicates an air gap (522) between the body and the patch sensor (590). The air gap will produce changes in the reactance sensed by the reactance sensors (520) and a processor can generate an alarm indicating that the physiological parameter sensor (510) may not obtain a proper reading or that the patch needs to be readjusted.

Figure 6:
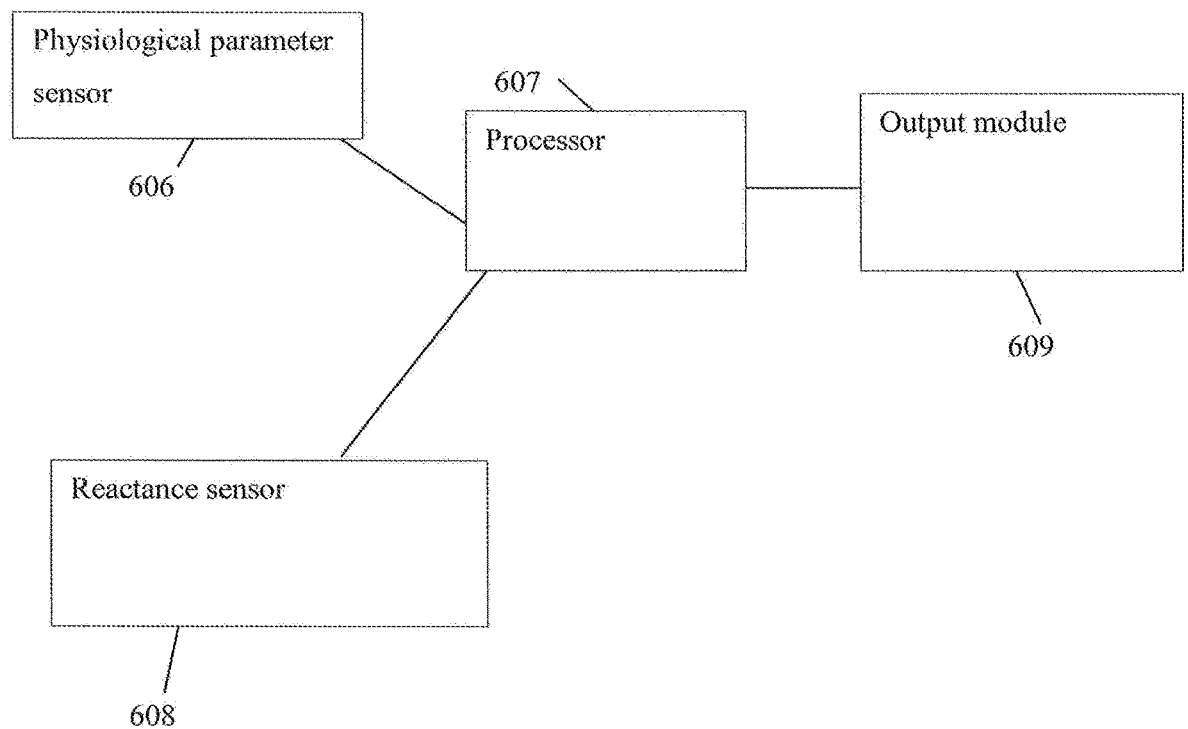
FIG. 6 illustrates an electrical diagram showing an example of a sensor circuit and the reactance sensing circuit.

FIG. 6 is an electrical schematic showing the connections and components of sensing system (605). In one example a physiological parameter sensor (606) and reactance sensor (608) are operatively coupled to a processor (607). The processor is operatively coupled to an output module (609). In one example, the sensors, processor and output module can be in a single housing. In other embodiments, the sensors can be remotely connected by cable or wirelessly to a processor and an output module.

Figure 7:
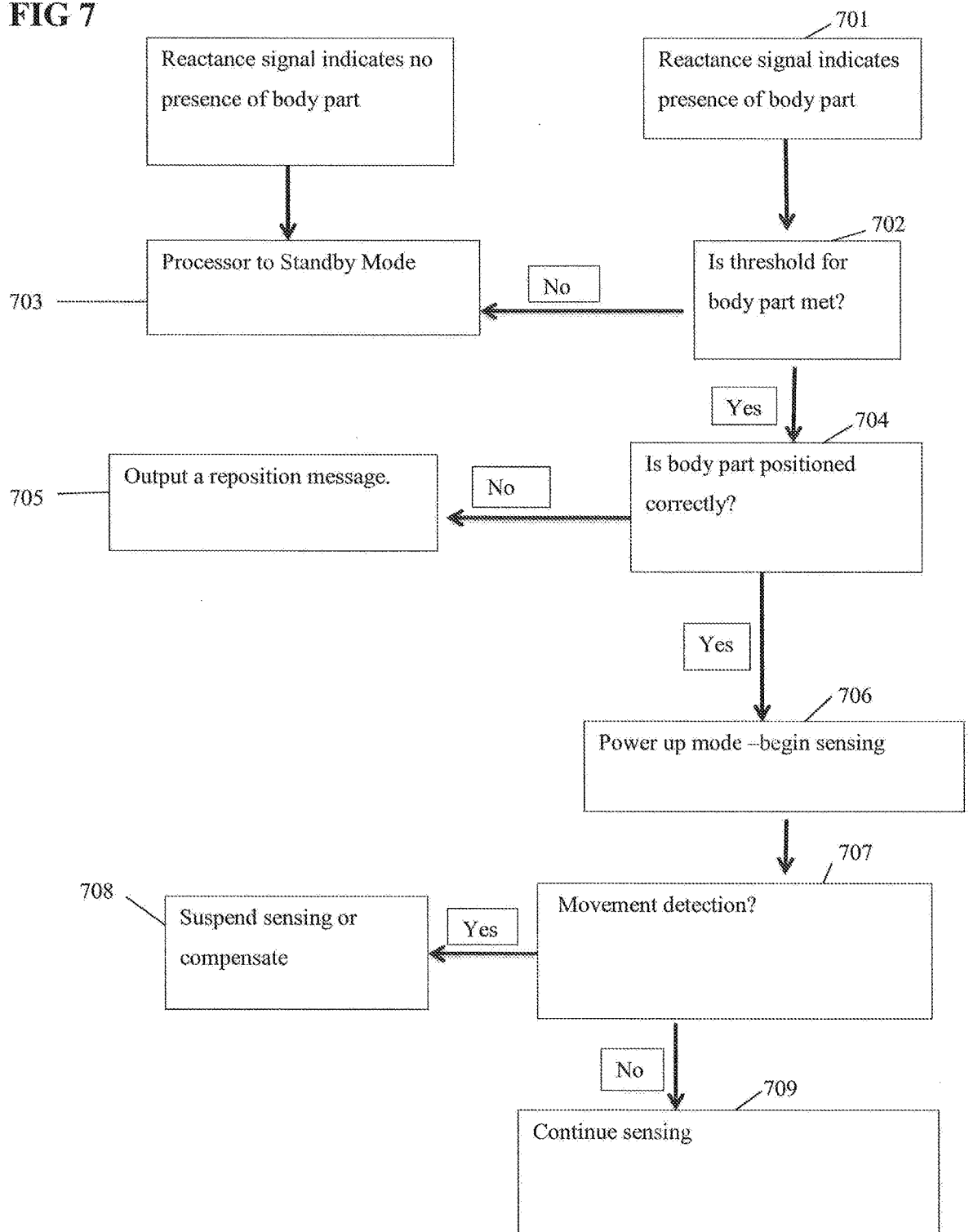
FIG. 7 illustrates a method or software flowchart showing system operations.

FIG. 7 illustrates flowchart 700 corresponding to a method or software algorithm of a mode of operation. At 701, a reactance signal indicates the presence of a body part. At 702, the processor is instructed to determine whether the signal threshold for a body part has been met. At 703, if the answer is "no" the processor is instructed to operate in standby mode until a further instruction to power up or power off. At 704, if the answer is "yes" it is then a determination is made on whether a body part is positioned correctly. At 705, if it is determined that the body part is not correctly positioned, the output module is instructed to generate a reposition message. At 706, if the body part is positioned correctly the processor is instructed to initiate a power up mode and begin physiological parameter sensing. At 707, as the physiological parameter sensing proceeds, the reactance sensor may sense movement. At 708, the processor can be instructed to suspend sensing or compensate for movement. At 709, if no movement is sensed by the reactance sensor, the processor can be instructed to continue physiological parameter sensing.

A body part alters the electrical field generated by a reactance sensor. The reactance sensor generates a signal to the processor. The processing software has threshold lookup tables which can determine if the received signal actually indicates a body part and whether the body part has reached a proper location. If a threshold has been reached the software will initiate such processes as power up and processing physiological parameter sensor data. This threshold table maybe a single sensor threshold value that triggers a response when the reactance signal has exceeded the predetermined value. An alternative to the single sensor threshold that may be used is one or more algebraic equations to govern the interaction of multiple signals from multiple reactance sensors to establish a complex multidimensional value which must be exceeded.

Figure 8:
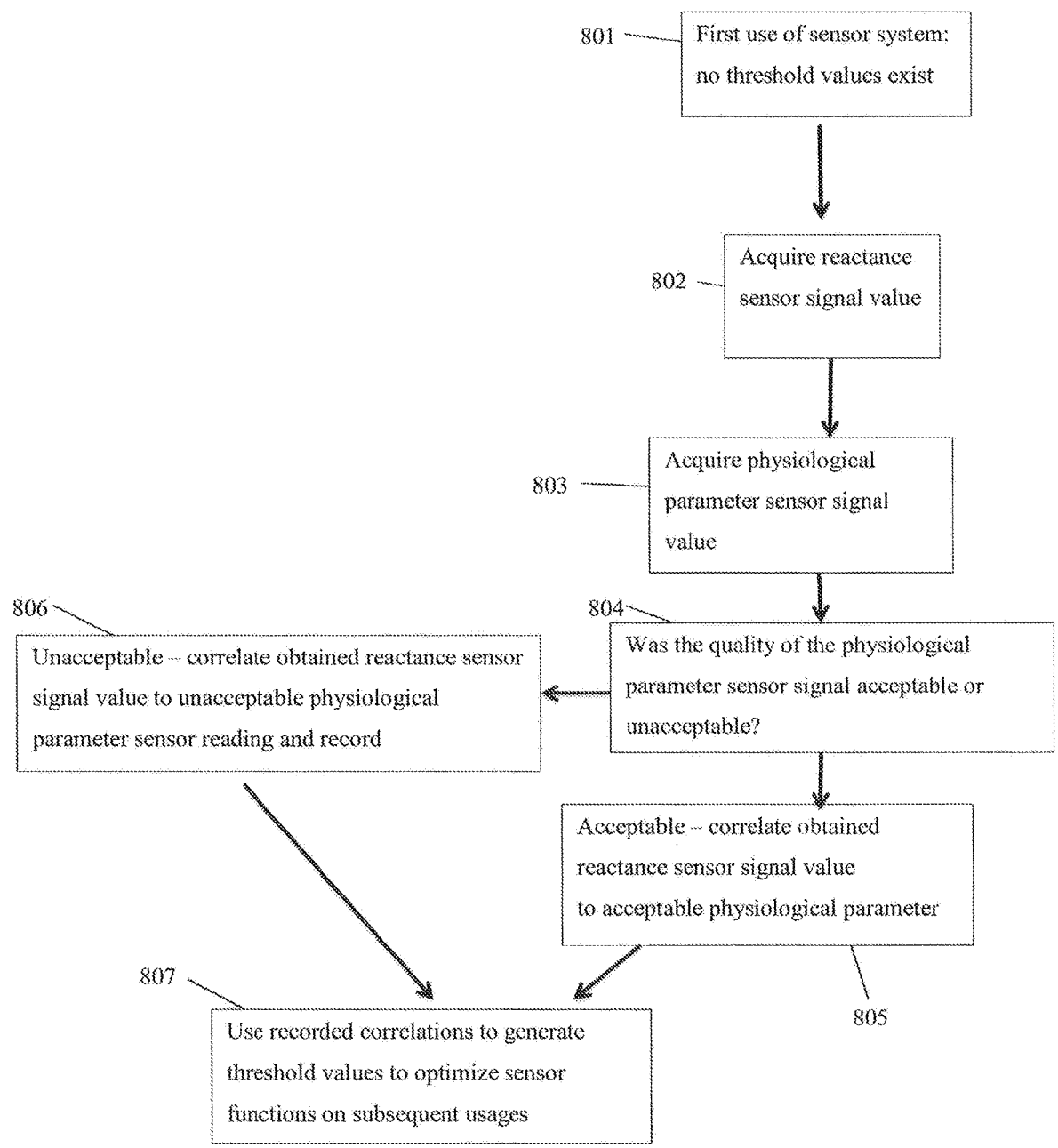
FIG. 8 illustrates a method or software flowchart showing system operations.

FIG. 8 illustrates flowchart 800 corresponding to a method or software algorithm of a mode of operation. In this mode a predetermined threshold, whether simple or multidimensional, is not used, but rather upon first usage the sensor system has no threshold value but during usage learns the correlation between reactance sensor signal value, whether simple or multidimensional, and physiological sensor signal quality. Upon subsequent use the sensor system uses a reactance sensor threshold that has in previous use correlated to a high physiological sensor signal quality to indicate adequate proximity between the body part and sensor. In FIG. 8 a first use of a sensor system is illustrated and, at 801, no threshold values have been established. At 802, a processor acquires a reactance sensor signal value. At 803, the processor acquires a physiological parameter sensor signal value. At 804, the processor is instructed to determine whether or not the quality of physiological parameter sensor signal is acceptable or unacceptable. At 805, if the quality of physiological parameter sensor signal is acceptable, the processor is instructed to correlate the obtained reactance signal to an acceptable physiological parameter sensor signal. At 806, if the quality of physiological parameter sensor signal is unacceptable, the processor is instructed to correlate the obtained reactance signal to an unacceptable physiological parameter sensor signal. At 807, the processor is instructed to use the correlations to provide threshold values which can be used to optimize sensor functions on subsequent usages.

Figure 9:
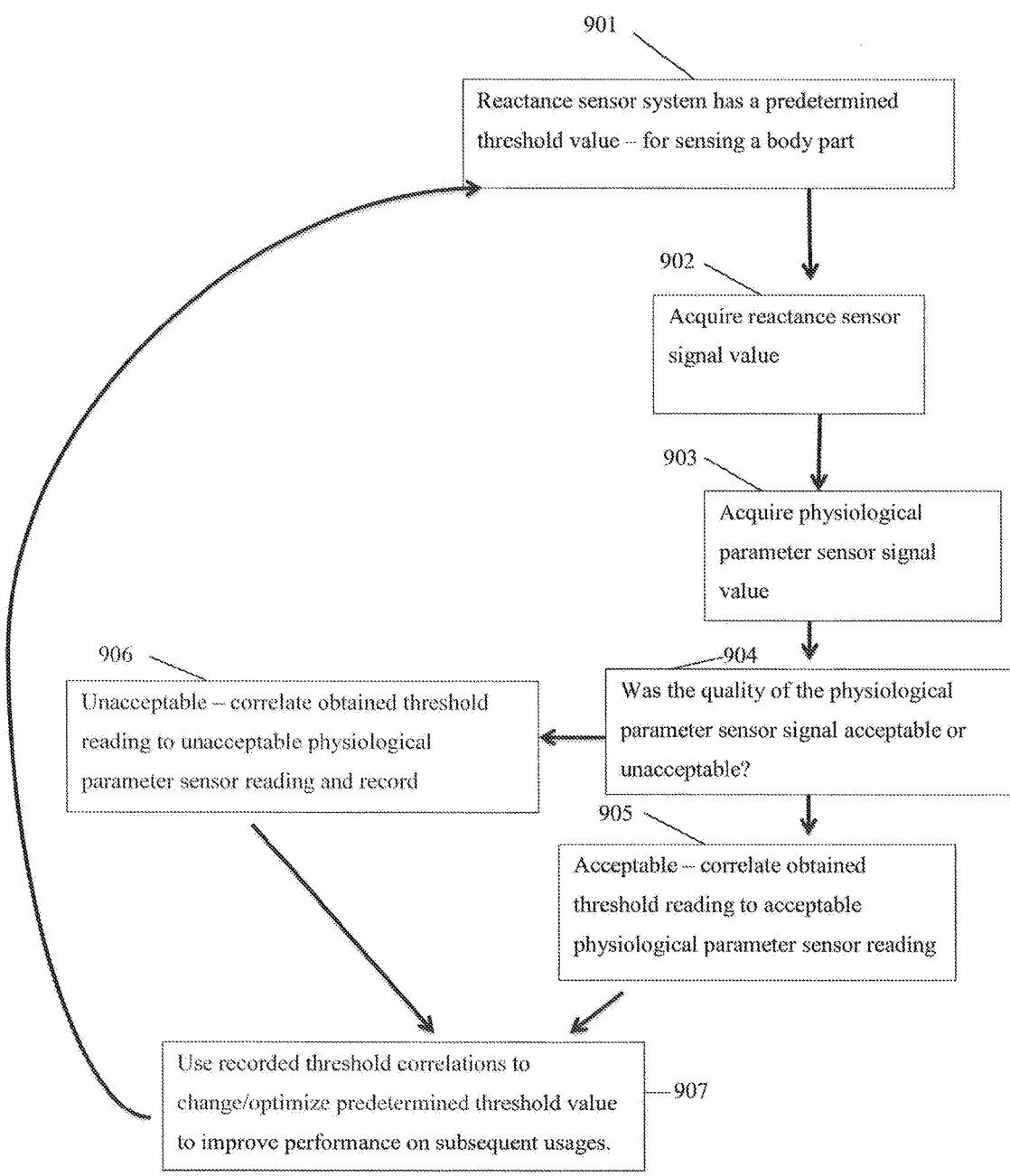
FIG. 9 illustrates a method or software flowchart showing system operations.

FIG. 9 illustrates flowchart 900 corresponding to a method or software algorithm of a mode of operation. In this mode the system starts with a predetermined reactance sensor threshold value, whether simple or multidimensional, but changes that threshold value overtime as it learns the correlation between reactance sensor signal values and physiological sensor signal quality. In FIG. 9 a reactance sensor system, at 901, has a predetermined threshold value for sensing a body part. At 902, a processor acquires a reactance sensor signal value. At 903, the processor acquires a physiological parameter sensor signal value. At 904, the processor is instructed to determine whether or not the quality of physiological parameter sensor signal is acceptable or unacceptable. At 905, if the quality of physiological parameter sensor signal is acceptable, the processor is instructed to correlate the obtained reactance signal to an acceptable physiological parameter sensor signal. At 906, if the quality of physiological parameter sensor signal is unacceptable, the processor is instructed to correlate the obtained reactance signal to an unacceptable physiological parameter sensor signal. At 907, the processor is instructed to use the correlations to change and/or optimize a predetermined threshold value which can be used to optimize sensor functions on subsequent usages.

Figure 10:
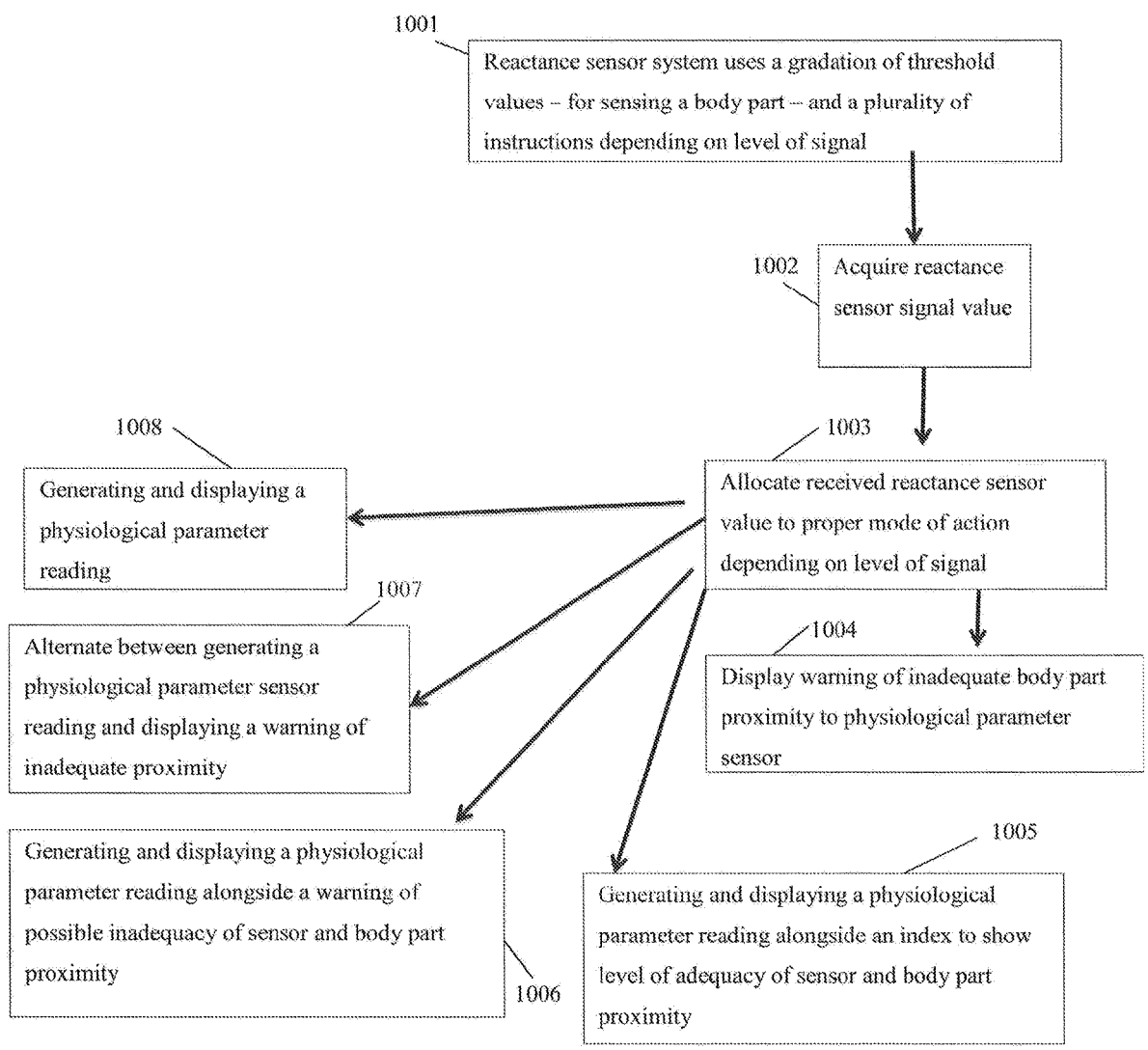
FIG. 10 illustrates a method or software flowchart showing system operations.

FIG. 10 illustrates flowchart 1000 corresponding to a method or software algorithm of a mode of operation. In this mode the system uses a gradation of threshold values to determine mode of operation. The system may have several modes of operation upon finger insertion which are determined by reactance sensor signal values. These modes of operation may include but not be limited to: displaying only a warning of inadequate sensor and body part proximity; alternating between generating and displaying a physiological reading and displaying a warning of possible inadequate sensor and body part proximity; generating and displaying a physiological reading alongside an index to show level of adequacy of sensor and body part proximity; generating and displaying a physiological reading alongside a warning of possible inadequacy of sensor and body part proximity and generating and displaying a physiological reading.

At 1001, FIG. 10 illustrates a reactance sensing system that uses a gradation of threshold values—for sensing a body part—and a plurality of instructions depending on level of signal. At 1002, a processor is instructed to acquire a reactance sensor signal value. Depending on the gradation of threshold values, the processor is instructed to allocate, at 1003, a received reactance sense value to a proper mode of action depending on level of signal and initiate a function not limited to the following functions: a) display warning of inadequate body part proximity to physiological parameter sensor at 1004, b) generating and displaying a physiological parameter reading alongside an index to show level of adequacy of sensor and body part proximity at 1005, c) generating and displaying a physiological parameter reading alongside a warning of possible inadequacy of sensor and body part proximity at 1006, d) alternate between generating a physiological parameter sensor reading and displaying a warning of inadequate proximity at 1007, and e) generating and displaying a physiological parameter reading at 1008.

Figure 11:
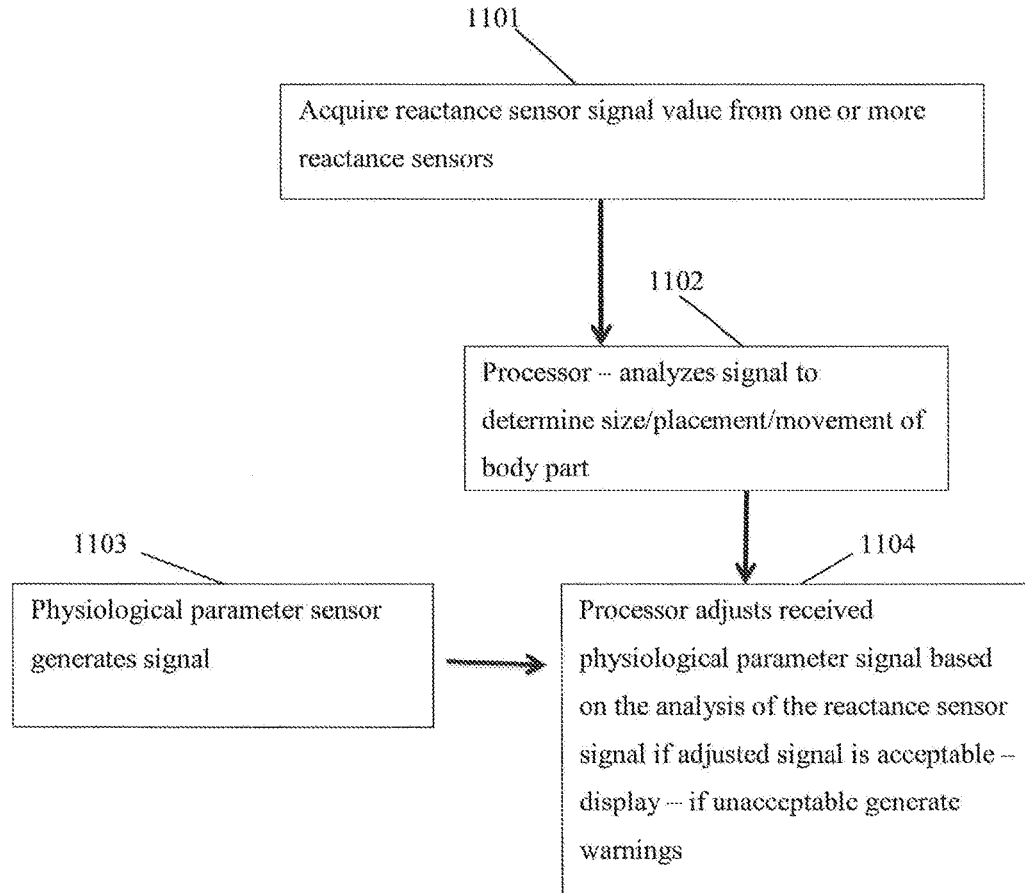
FIG. 11 illustrates a method or software flowchart showing system operations.

FIG. 11 illustrates flowchart 1100 corresponding to a method or software algorithm of a mode of operation. In this mode the system uses one or more reactance sensor signals to modify the data obtained from the physiological sensor. The adjustment of physiological sensor data could include, but is not limited to compensation for body part movement, body part size, or body part placement. At 1101, a processor is instructed to acquire reactance sensor signal values from one or more reactance sensors. At 1102, the processor is instructed to analyze the signal to determine size/placement/movement of a body part. After the software instructs the processor to receive a physiological parameter sensor signal, at 1103, the software instructs the processor to adjust the physiological parameter signal based on the analysis of the reactance sensor signal. At 1104, if the adjusted physiological parameter signal is acceptable—display readings;—if unacceptable generate warnings.

FIG. 12 illustrates flowchart 1200 corresponding to a method or software algorithm of a mode of operation. In this mode the system uses signals from one or more reactance sensors to provide body part location information to the user through an output module in order to assist the user in optimal sensor placement. The output module can generate output with a visual signal, with an audio signal or a combination of both an audio and visual signal. At 1201, a processor is instructed to acquire reactance sensor signal value from one or more reactance sensors. At 1202, a processor is then instructed analyze the signal to determine proximity of a body part to a physiological parameter sensor. At 1203, based on the proximity determination, the processor is instructed to supply output module messages which direct the user of the sensing system. At 1204, the output module displays directions based on reactance sensing and/or physiological parameter sensing readings/correlations. Example directions are a) "Insert finger farther into sensor", at 1205, b) "Stop moving finger", at 1206, or c) "Move finger to the left", at 1207.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed:

1. A sensor assembly including:
   a first physiological parameter sensor configured to sense a physiological parameter;
   a phased array of reactance sensors including a first reactance sensor and a second reactance sensor, the array of reactance sensors connected to the first physiological parameter sensor wherein the array provides a signal corresponding to a position of a tissue relative to the first reactance sensor and relative to the first physiological parameter sensor; and wherein the first reactance sensor includes at least one of a capacitor and an inductor;
   a processor coupled to the first physiological parameter sensor and coupled to the array, the processor configured to select an operational mode for the first physiological parameter sensor based upon the signal provided by the array, wherein the processor is configured to generate an output based on the physiological parameter and the position if the signal provided by the array exceeds a threshold value.

2. The sensor assembly of claim 1, wherein the first physiological parameter sensor is configured to be controlled by signals generated by the reactance sensor.

3. The sensor assembly of claim 1, wherein the first reactance sensor and the second reactance sensor are in fixed positions relative to the first physiological parameter sensor.

4. The sensor assembly of claim 1 further including a second physiological parameter sensor coupled to the first reactance sensor.

5. The sensor assembly of claim 1, wherein the first physiological parameter sensor includes at least one of a pulse oximetry sensor, a tissue oximetry sensor, a temperature sensor, a blood pressure sensor, a blood analyte sensor, a respiratory rate sensor, and a capnography sensor.

6. The sensor assembly of claim 1 wherein the first physiological parameter sensor includes a multifunction sensor configured to measure any combination of pulse, saturated oxygen content, blood pressure, body temperature, blood analyte concentration, respiratory gas concentration, and breathing rate.

7. The sensor assembly of claim 1 configured to receive at least one of a fingertip, a toe, an ear lobe, an arm, a wrist, and a foot.

8. The sensor assembly of claim 1 wherein the sensor assembly has a planar planform.

9. A non-transitory computer readable medium comprising machine readable information for causing a machine to:
   read physiological parameter sensor data and reactance sensor data, wherein the physiological parameter sensor data is from a first physiological parameter sensor configured to sense a physiological parameter and the reactance sensor data is from a phased array of reactance sensors including a first reactance sensor and a second reactance sensor, the array of reactance sensors connected to the first physiological parameter sensor, wherein the array provides a signal corresponding to a position of a tissue relative to the first reactance sensor and relative to the first physiological parameter sensor; and wherein the first reactance sensor includes at least one of a capacitor and an inductor;

select an operation mode for the first physiological parameter sensor based upon the signal provided by the array; and output physiological parameter data based on the physiological parameter and the position if the signal provided by the array exceeds a threshold value.

10. The computer readable medium of claim 9 wherein the computer readable medium is configured to:

compare the reactance sensor data to the threshold value; and determine a position of the first reactance sensor and the first physiological parameter sensor relative to the tissue based on the comparison.

11. The computer readable medium of claim 9, wherein the computer readable medium is configured to:

compare the reactance sensor data to a threshold lookup table;

compare the physiological parameter sensor data with a stored value; and generate a result based on the comparison of the reactance sensor data and the comparison of the physiological parameter sensor data.

12. A method of using a sensor assembly comprising:

providing a first physiological parameter sensor configured to sense a physiological parameter;

generating a reactance sensing signal with a phased array of reactance sensors including a first reactance sensor and a second reactance sensor, wherein the reactance sensing signal corresponds to a position of a tissue relative to the first reactance sensor and relative to the first physiological parameter sensor; and wherein the first reactance sensor includes at least one of a capacitor and an inductor;

determining a value of the reactance sensing signal;

comparing the reactance sensing signal to a threshold value;

selecting an operation mode for the first physiological parameter sensor based upon the signal provided by the array; and based upon the comparing, generating a physiological parameter sensor signal indicative of the physiological parameter exceeds the threshold value.

13. The method of claim 12, further comprising determining a quality of the physiological parameter sensor signal.

14. The method of claim 13, further comprising setting the threshold value for the reactance sensing signal using information about the determined quality of the physiological parameter sensor signal.

15. The method of claim 12, further comprising altering the physiological parameter sensor signal using information about the reactance sensing signal.

16. The method of claim 12, further comprising providing a user-detectable indication of the position of the tissue relative to the first reactance sensor and relative to the first physiological parameter sensor based upon the comparison between the reactance sensing signal and the threshold value.

* * * * *